US005350576A

United States Patent [19]

Payne et al.

[11] Patent Number: 5,350,576

[45] **Date of Patent: * Sep. 27, 1994**

[54] ***BACILLUS THURINGIENSIS* ISOLATES FOR CONTROLLING ACARIDES**

[75] Inventors: Jewel Payne, San Diego, Calif.; Raymond J. C. Cannon; Angela L. Ralph, both of Kent, Great Britain

[73] Assignee: Mycogen Corporation, San Diego, Calif.

[*] Notice: The portion of the term of this patent subsequent to May 18, 2010 has been disclaimed.

[21] Appl. No.: 63,170

[22] Filed: May 17, 1993

Related U.S. Application Data

[63] Continuation-in-part of Ser. No. 768,141, Sep. 30, 1991, Pat. No. 5,211,946, which is a continuation-in-part of Ser. No. 759,248, Sep. 13, 1991, abandoned.

[51] Int. Cl.$^5$ .................... A01N 61/00; C12N 1/20; C07K 15/02

[52] U.S. Cl. .................... 424/93.461; 424/405; 424/93.46; 424/93.4; 435/252.5; 435/832; 514/2; 514/12; 530/350; 530/825; 935/63; 935/64; 536/23.71

[58] Field of Search .................... 424/93 R, 93 A, 93 K, 424/93 L, 405; 435/252.3, 252.31, 252.5, 832

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,797,276 | 1/1989 | Herrnstadt et al. | 424/84 |
| 4,849,217 | 7/1989 | Soares et al. | 424/93 L |
| 4,853,331 | 8/1989 | Herrnstadt et al. | 435/252.3 |
| 4,948,734 | 8/1990 | Edwards et al. | 435/252.5 |
| 5,064,648 | 11/1991 | Hickle et al. | |
| 5,093,120 | 3/1992 | Edwards et al. | 424/93 L |
| 5,211,946 | 5/1993 | Payne et al. | 424/93 L |

OTHER PUBLICATIONS

Biol. Abstract No. 15427. (Saleh et al. 1991. Acarologia, vol. 33, No. 2, pp. 257–260) vol. 93, No. 2, Jan. 15, 1992.

Royalty, Reed N., Franklin R. Hall, and R. A. J. Taylor (1990) "Effect of Thuringiensin on *Tetranychus urticae* (Acari: Tetranychidae) Mortality, Fecundity, and Feeding" Journal of Economic Entomology 83:792–798.

Neal, John W., Jr., Richard K. Lindquist, K. M. Gott, and M. L., Casey (1987) "Activity of the Thermostable $\beta$-Exotoxin of *Bacillus thuringiensis* Berliner on *Tetranychus Urticae* and *T. Cinnabarinus*" J. Agric. Entomol. 4(1):33–40.

Vlayen, P., G. Van, R. Semaille (1978) "Activate D'Une Preparation Commerciale de *Bacillus thuringiensis* Sur L'Acarien Tisserand Commun *Tetranychus Urticae* Koch. (Acari: Tetranychidae)" Med. Fac. Landbouww, Rijksuniv. Cent. 43(2):471–479.

Gaertner, Frank, and Leo Kim (1988) "Current Applied Recombinant DNA Projects" Tibtech 6(4):S4–S7.

Gaertner, Frank (1990) "Cellular Delivery Systems for Insecticidal Proteins: Living and Non–Living Microorganisms" Controlled Delivery of Crop–Protection Agents R. M. Wilkins, ed., Taylor and Francis, New York and London, pp. 245–255.

Hofte, Herman, and H. R. Whiteley (1989) "Insecticidal Crystal Proteins of *Bacillus thuringiensis*" Microbiological Reviews 53(2):242–255.

Feitelson, Jerald S., Jewel Payne, and Leo Kim (1992) "*Bacillus thuringiensis:* Insects and Beyond" Bio/Technology 10:271–275.

(List continued on next page.)

*Primary Examiner*—Christopher S. F. Low
*Attorney, Agent, or Firm*—Saliwanchik & Saliwanchik

[57] ABSTRACT

Disclosed are *Bacillus thuringiensis* isolates designated B.t. PS45B1, B.t. PS24J, B.t. PS94R3 B.t. PS17, B.t. PS62B1 and B.t. PS74G1 which produce novel δ-endotoxins active against acarid pests. Thus, these isolates, or mutants thereof, can be used to control such pests. Claimed are genes encoding these novel δ-endotoxins, which can be removed from these isolates and transferred to other host microbes, or plants. Expression of the toxins in microbe hosts results in the control of acarid pests, whereas transformed plants become resistant to acarid pests.

8 Claims, 1 Drawing Sheet

OTHER PUBLICATIONS

Schnepf, H. Ernest, and H. R. Whiteley (1981) "Cloning and Expression of the *Bacillus thuringiensis* Crystal Protein Gene in *Escherichia coli*" Proc. Natl. Acad. Sci. USA 78(5):2893–2897.
Kreig, Von A., A. M. Huger, G. A. Langenbruch, and W. Schnetter (1983) "*Bacillus thuringiensis* var. *temebrionis*:ein neuer, gegenuber Larven von Coleopteren wirksamer Pathotyp" Z. ang. Ent. 96:500–508.
Couch, T. L. (1980) "Mosquito Pathogenicity of *Bacillus thuringiensis* var. *israelensis*" Developments in Industrial Microbiology 22:61–76.
Beegle, C. C. (1978) "Use of Entomogenous Bacteria in Agroecosystems" Developments in Industrial Microbiology 20:97–104.

A. *Bacillus thuringiensis* PS24J
B. *Bacillus thuringiensis* PS94R3
C. *Bacillus thuringiensis* PS45B1
D. *Bacillus thuringiensis* PS17
E. *Bacillus thuringiensis* PS62B1
F. *Bacillus thuringiensis* PS74C1

SEQUENCE LISTING ( 1 ) GENERAL INFORMATION:

( i i i ) NUMBER OF SEQUENCES: 4

-continued ( 2 ) INFORMATION FOR SEQ ID NO:1:

( i ) SEQUENCE CHARACTERISTICS:
( A ) LENGTH: 4155 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: PS17
( C ) INDIVIDUAL ISOLATE: PS17a ( x i ) SEQUENCE DESCRIPTION: SEQ ID NO:1:

ATGGCAATTT TAAATGAATT ATATCCATCT GTACCTTATA ATGTATTGGC GTATACGCCA 60
CCCTCTTTTT TACCTGATGC GGGTACACAA GCTACACCTG CTGACTTAAC AGCTTATGAA 120
CAATTGTTGA AAAATTTAGA AAAAGGGATA AATGCTGGAA CTTATTCGAA AGCAATAGCT 180
GATGTACTTA AAGGTATTTT TATAGATGAT ACAATAAATT ATCAAACATA TGTAAATATT 240
GGTTTAAGTT TAATTACATT AGCTGTACCG GAAATTGGTA TTTTTACACC TTTCATCGGT 300
TTGTTTTTTG CTGCATTGAA TAAACATGAT GCTCCACCTC CTCCTAATGC AAAAGATATA 360
TTTGAGGCTA TGAAACCAGC GATTCAAGAG ATGATTGATA GAACTTTAAC TGCGGATGAG 420
CAAACATTTT TAAATGGGGA AATAAGTGGT TTACAAAATT TAGCAGCAAG ATACCAGTCT 480
ACAATGGATG ATATTCAAAG CCATGGAGGA TTTAATAAGG TAGATTCTGG ATTAATTAAA 540
AAGTTTACAG ATGAGGTACT ATCTTTAAAT AGTTTTTATA CAGATCGTTT ACCTGTATTT 600
ATTACAGATA ATACAGCGGA TCGAACTTTG TTAGGTCTTC CTTATTATGC TATACTTGCG 660
AGCATGCATC TTATGTTATT AAGAGATATC ATTACTAAGG GTCCGACATG GGATTCTAAA 720
ATTAATTTCA CACCAGATGC AATTGATTCC TTTAAAACCG ATATTAAAAA TAATATAAAG 780
CTTTACTCTA AAACTATTTA TGACGTATTT CAGAAGGGAC TTGCTTCATA CGGAACGCCT 840
TCTGATTTAG AGTCCTTTGC AAAAAAACAA AAATATATTG AAATTATGAC AACACATTGT 900
TTAGATTTTG CAAGATTGTT TCCTACTTTT GATCCAGATC TTTATCCAAC AGGATCAGGT 960
GATATAAGTT TACAAAAAAC ACGTAGAATT CTTTCTCCTT TTATCCCTAT ACGTACTGCA 1020
GATGGGTTAA CATTAAATAA TACTTCAATT GATACTTCAA ATTGGCCTAA TTATGAAAAT 1080
GGGAATGGCG CGTTTCCAAA CCCAAAAGAA AGAATATTAA AACAATTCAA ACTGTATCCT 1140
AGTTGGAGAG CGGGACAGTA CGGTGGGCTT TTACAACCTT ATTTATGGGC AATAGAAGTC 1200
CAAGATTCTG TAGAGACTCG TTTGTATGGG CAGCTTCCAG CTGTAGATCC ACAGGCAGGG 1260
CCTAATTATG TTTCCATAGA TTCTTCTAAT CCAATCATAC AAATAAATAT GGATACTTGG 1320
AAAACACCAC CACAAGGTGC GAGTGGGTGG AATACAAATT TAATGAGAGG AAGTGTAAGC 1380
GGGTTAAGTT TTTTACAACG AGATGGTACG AGACTTAGTG CTGGTATGGG TGGTGGTTTT 1440
GCTGATACAA TATATAGTCT CCCTGCAACT CATTATCTTT CTTATCTCTA TGGAACTCCT 1500
TATCAAACTT CTGATAACTA TTCTGGTCAC GTTGGTGCAT TGGTAGGTGT GAGTACGCCT 1560
CAAGAGGCTA CTCTTCCTAA TATTATAGGT CAACCAGATG AACAGGGAAA TGTATCTACA 1620
ATGGGATTTC CGTTTGAAAA AGCTTCTTAT GGAGGTACAG TTGTTAAAGA ATGGTTAAAT 1680
GGTGCGAATG CGATGAAGCT TTCTCCTGGG CAATCTATAG GTATTCCTAT TACAAATGTA 1740
ACAAGTGGAG AATATCAAAT TCGTTGTCGT TATGCAAGTA ATGATAATAC TAACGTTTTC 1800

-continued

```
TTTAATGTAG ATACTGGTGG AGCAAATCCA ATTTTCCAAC AGATAAACTT TGCATCTACT 1860
GTAGATAATA ATACGGGAGT ACAAGGAGCA AATGGTGTCT ATGTAGTCAA ATCTATTGCT 1920
ACAACTGATA ATTCTTTTAC AGAAATTCCT GCGAAGACGA TTAATGTTCA TTTAACCAAC 1980
CAAGGTTCTT CTGATGTCTT TTTAGACCGT ATTGAATTTA TACCTTTTTC TCTACCTCTT 2040
ATATATCATG GAAGTTATAA TACTTCATCA GGTGCAGATG ATGTTTTATG GTCTTCTTCA 2100
AATATGAATT ACTACGATAT AATAGTAAAT GGTCAGGCCA ATAGTAGTAG TATCGCTAGT 2160
TCTATGCATT TGCTTAATAA AGGAAAAGTG ATAAAAACAA TTGATATTCC AGGGCATTCG 2220
GAAACCTTCT TTGCTACGTT CCCAGTTCCA GAAGGATTTA ATGAAGTTAG AATTCTTGCT 2280
GGCCTTCCAG AAGTTAGTGG AAATATTACC GTACAATCTA ATAATCCGCC TCAACCTAGT 2340
AATAATGGTG GTGGTGATGG TGGTGGTAAT GGTGGTGGTG ATGGTGGTCA ATACAATTTT 2400
TCTTTAAGCG GATCTGATCA TACGACTATT TATCATGGAA AACTTGAAAC TGGGATTCAT 2460
GTACAAGGTA ATTATACCTA TACAGGTACT CCCGTATTAA TACTGAATGC TTACAGAAAT 2520
AATACTGTAG TATCAAGCAT TCCAGTATAT TCTCCTTTTG ATATAACTAT ACAGACAGAA 2580
GCTGATAGCC TTGAGCTTGA ACTACAACCT AGATATGGTT TTGCCACAGT GAATGGTACT 2640
GCAACAGTAA AAAGTCCTAA TGTAAATTAC GATAGATCAT TTAAACTCCC AATAGACTTA 2700
CAAAATATCA CAACACAAGT AAATGCATTA TTCGCATCTG GAACACAAAA TATGCTTGCT 2760
CATAATGTAA GTGATCATGA TATTGAAGAA GTTGTATTAA AAGTGGATGC CTTATCAGAT 2820
GAAGTATTTG GAGATGAGAA GAAGGCTTTA CGTAAATTGG TGAATCAAGC AAAACGTTTG 2880
AGTAGAGCAA GAAATCTTCT GATAGGTGGG AGTTTTGAAA ATTGGGATGC ATGGTATAAA 2940
GGAAGAAATG TAGTAACTGT ATCTGATCAT GAACTATTTA AGAGTGATCA TGTATTATTA 3000
CCACCACCAG GATTGTCTCC ATCTTATATT TTCCAAAAAG TGGAGGAATC TAAATTAAAA 3060
CCAAATACAC GTTATATTGT TTCTGGATTC ATCGCACATG GAAAAGACCT AGAAATTGTT 3120
GTTTCACGTT ATGGGCAAGA AGTGCAAAAG GTCGTGCAAG TTCCTTATGG AGAAGCATTC 3180
CCGTTAACAT CAAATGGACC AGTTTGTTGT CCCCCACGTT CTACAAGTAA TGGAACCTTA 3240
GGAGATCCAC ATTTCTTTAG TTACAGTATC GATGTAGGTG CACTAGATTT ACAAGCAAAC 3300
CCTGGTATTG AATTTGGTCT TCGTATTGTA AATCCAACTG GAATGGCACG CGTAAGCAAT 3360
TTGGAAATTC GTGAAGATCG TCCATTAGCA GCAAATGAAA TACGACAAGT ACAACGTGTC 3420
GCAAGAAATT GGAGAACCGA GTATGAGAAA GAACGTGCGG AAGTAACAAG TTTAATTCAA 3480
CCTGTTATCA ATCGAATCAA CGGATTGTAT GAAAATGGAA ATTGGAACGG TTCTATTCGT 3540
TCAGATATTT CGTATCAGAA TATAGACGCG ATTGTATTAC CAACGTTACC AAAGTTACGC 3600
CATTGGTTTA TGTCAGATAG ATTCAGTGAA CAAGGAGATA TAATGGCTAA ATTCCAAGGT 3660
GCATTAAATC GTGCGTATGC ACAACTGGAA CAAAGTACGC TTCTGCATAA TGGTCATTTT 3720
ACAAAAGATG CAGCTAATTG GACAATAGAA GGCGATGCAC ATCAGATAAC ACTAGAAGAT 3780
GGTAGACGTG TATTGCGACT TCCAGATTGG TCTTCGAGTG TATCTCAAAT GATTGAAATC 3840
GAGAATTTTA ATCCAGATAA AGAATACAAC TTAGTATTCC ATGGGCAAGG AGAAGGAACG 3900
GTTACGTTGG AGCATGGAGA AGAAACAAAA TATATAGAAA CGCATACACA TCATTTTGCG 3960
AATTTTACAA CTTCTCAACG TCAAGGACTC ACGTTTGAAT CAAATAAAGT GACAGTGACC 4020
ATTTCTTCAG AAGATGGAGA ATTCTTAGTG GATAATATTG CGCTTGTGGA AGCTCCTCTT 4080
CCTACAGATG ACCAAAATTC TGAGGGAAAT ACGGCTTCCA GTACGAATAG CGATACAAGT 4140
ATGAACAACA ATCAA                                                   4155
```

-continued ( 2 ) INFORMATION FOR SEQ ID NO:2:

( i ) SEQUENCE CHARACTERISTICS:
( A ) LENGTH: 1385 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: PS17
( C ) INDIVIDUAL ISOLATE: PS17a ( x i ) SEQUENCE DESCRIPTION: SEQ ID NO:2:

Met Ala Ile Leu Asn Glu Leu Tyr Pro Ser Val Pro Tyr Asn Val Leu
1 5 10 15

Ala Tyr Thr Pro Pro Ser Phe Leu Pro Asp Ala Gly Thr Gln Ala Thr
20 25 30

Pro Ala Asp Leu Thr Ala Tyr Glu Gln Leu Leu Lys Asn Leu Glu Lys
35 40 45

Gly Ile Asn Ala Gly Thr Tyr Ser Lys Ala Ile Ala Asp Val Leu Lys
50 55 60

Gly Ile Phe Ile Asp Asp Thr Ile Asn Tyr Gln Thr Tyr Val Asn Ile
65 70 75 80

Gly Leu Ser Leu Ile Thr Leu Ala Val Pro Glu Ile Gly Ile Phe Thr
85 90 95

Pro Phe Ile Gly Leu Phe Phe Ala Ala Leu Asn Lys His Asp Ala Pro
100 105 110

Pro Pro Pro Asn Ala Lys Asp Ile Phe Glu Ala Met Lys Pro Ala Ile
115 120 125

Gln Glu Met Ile Asp Arg Thr Leu Thr Ala Asp Glu Gln Thr Phe Leu
130 135 140

Asn Gly Glu Ile Ser Gly Leu Gln Asn Leu Ala Ala Arg Tyr Gln Ser
145 150 155 160

Thr Met Asp Asp Ile Gln Ser His Gly Gly Phe Asn Lys Val Asp Ser
165 170 175

Gly Leu Ile Lys Lys Phe Thr Asp Glu Val Leu Ser Leu Asn Ser Phe
180 185 190

Tyr Thr Asp Arg Leu Pro Val Phe Ile Thr Asp Asn Thr Ala Asp Arg
195 200 205

Thr Leu Leu Gly Leu Pro Tyr Tyr Ala Ile Leu Ala Ser Met His Leu
210 215 220

Met Leu Leu Arg Asp Ile Ile Thr Lys Gly Pro Thr Trp Asp Ser Lys
225 230 235 240

Ile Asn Phe Thr Pro Asp Ala Ile Asp Ser Phe Lys Thr Asp Ile Lys
245 250 255

Asn Asn Ile Lys Leu Tyr Ser Lys Thr Ile Tyr Asp Val Phe Gln Lys
260 265 270

Gly Leu Ala Ser Tyr Gly Thr Pro Ser Asp Leu Glu Ser Phe Ala Lys
275 280 285

Lys Gln Lys Tyr Ile Glu Ile Met Thr Thr His Cys Leu Asp Phe Ala
290 295 300

Arg Leu Phe Pro Thr Phe Asp Pro Asp Leu Tyr Pro Thr Gly Ser Gly
305 310 315 320

Asp Ile Ser Leu Gln Lys Thr Arg Arg Ile Leu Ser Pro Phe Ile Pro

-continued 325 330 335

Ile Arg Thr Ala Asp Gly Leu Thr Leu Asn Asn Thr Ser Ile Asp Thr
340 345 350

Ser Asn Trp Pro Asn Tyr Glu Asn Gly Asn Gly Ala Phe Pro Asn Pro
355 360 365

Lys Glu Arg Ile Leu Lys Gln Phe Lys Leu Tyr Pro Ser Trp Arg Ala
370 375 380

Gly Gln Tyr Gly Gly Leu Leu Gln Pro Tyr Leu Trp Ala Ile Glu Val
385 390 395 400

Gln Asp Ser Val Glu Thr Arg Leu Tyr Gly Gln Leu Pro Ala Val Asp
405 410 415

Pro Gln Ala Gly Pro Asn Tyr Val Ser Ile Asp Ser Ser Asn Pro Ile
420 425 430

Ile Gln Ile Asn Met Asp Thr Trp Lys Thr Pro Pro Gln Gly Ala Ser
435 440 445

Gly Trp Asn Thr Asn Leu Met Arg Gly Ser Val Ser Gly Leu Ser Phe
450 455 460

Leu Gln Arg Asp Gly Thr Arg Leu Ser Ala Gly Met Gly Gly Gly Phe
465 470 475 480

Ala Asp Thr Ile Tyr Ser Leu Pro Ala Thr His Tyr Leu Ser Tyr Leu
485 490 495

Tyr Gly Thr Pro Tyr Gln Thr Ser Asp Asn Tyr Ser Gly His Val Gly
500 505 510

Ala Leu Val Gly Val Ser Thr Pro Gln Glu Ala Thr Leu Pro Asn Ile
515 520 525

Ile Gly Gln Pro Asp Glu Gln Gly Asn Val Ser Thr Met Gly Phe Pro
530 535 540

Phe Glu Lys Ala Ser Tyr Gly Gly Thr Val Val Lys Glu Trp Leu Asn
545 550 555 560

Gly Ala Asn Ala Met Lys Leu Ser Pro Gly Gln Ser Ile Gly Ile Pro
565 570 575

Ile Thr Asn Val Thr Ser Gly Glu Tyr Gln Ile Arg Cys Arg Tyr Ala
580 585 590

Ser Asn Asp Asn Thr Asn Val Phe Phe Asn Val Asp Thr Gly Gly Ala
595 600 605

Asn Pro Ile Phe Gln Gln Ile Asn Phe Ala Ser Thr Val Asp Asn Asn
610 615 620

Thr Gly Val Gln Gly Ala Asn Gly Val Tyr Val Val Lys Ser Ile Ala
625 630 635 640

Thr Thr Asp Asn Ser Phe Thr Glu Ile Pro Ala Lys Thr Ile Asn Val
645 650 655

His Leu Thr Asn Gln Gly Ser Ser Asp Val Phe Leu Asp Arg Ile Glu
660 665 670

Phe Ile Pro Phe Ser Leu Pro Leu Ile Tyr His Gly Ser Tyr Asn Thr
675 680 685

Ser Ser Gly Ala Asp Asp Val Leu Trp Ser Ser Ser Asn Met Asn Tyr
690 695 700

Tyr Asp Ile Ile Val Asn Gly Gln Ala Asn Ser Ser Ser Ile Ala Ser
705 710 715 720

Ser Met His Leu Leu Asn Lys Gly Lys Val Ile Lys Thr Ile Asp Ile
725 730 735

Pro Gly His Ser Glu Thr Phe Phe Ala Thr Phe Pro Val Pro Glu Gly
740 745 750

Phe Asn Glu Val Arg Ile Leu Ala Gly Leu Pro Glu Val Ser Gly Asn
755 760 765

-continued

Ile Thr Val Gln Ser Asn Asn Pro Pro Gln Pro Ser Asn Asn Gly Gly
770 775 780

Gly Asp Gly Gly Gly Asn Gly Gly Gly Asp Gly Gly Gln Tyr Asn Phe
785 790 795 800

Ser Leu Ser Gly Ser Asp His Thr Thr Ile Tyr His Gly Lys Leu Glu
805 810 815

Thr Gly Ile His Val Gln Gly Asn Tyr Thr Tyr Thr Gly Thr Pro Val
820 825 830

Leu Ile Leu Asn Ala Tyr Arg Asn Asn Thr Val Val Ser Ser Ile Pro
835 840 845

Val Tyr Ser Pro Phe Asp Ile Thr Ile Gln Thr Glu Ala Asp Ser Leu
850 855 860

Glu Leu Glu Leu Gln Pro Arg Tyr Gly Phe Ala Thr Val Asn Gly Thr
865 870 875 880

Ala Thr Val Lys Ser Pro Asn Val Asn Tyr Asp Arg Ser Phe Lys Leu
885 890 895

Pro Ile Asp Leu Gln Asn Ile Thr Thr Gln Val Asn Ala Leu Phe Ala
900 905 910

Ser Gly Thr Gln Asn Met Leu Ala His Asn Val Ser Asp His Asp Ile
915 920 925

Glu Glu Val Val Leu Lys Val Asp Ala Leu Ser Asp Glu Val Phe Gly
930 935 940

Asp Glu Lys Lys Ala Leu Arg Lys Leu Val Asn Gln Ala Lys Arg Leu
945 950 955 960

Ser Arg Ala Arg Asn Leu Leu Ile Gly Gly Ser Phe Glu Asn Trp Asp
965 970 975

Ala Trp Tyr Lys Gly Arg Asn Val Val Thr Val Ser Asp His Glu Leu
980 985 990

Phe Lys Ser Asp His Val Leu Leu Pro Pro Pro Gly Leu Ser Pro Ser
995 1000 1005

Tyr Ile Phe Gln Lys Val Glu Glu Ser Lys Leu Lys Pro Asn Thr Arg
1010 1015 1020

Tyr Ile Val Ser Gly Phe Ile Ala His Gly Lys Asp Leu Glu Ile Val
1025 1030 1035 1040

Val Ser Arg Tyr Gly Gln Glu Val Gln Lys Val Val Gln Val Pro Tyr
1045 1050 1055

Gly Glu Ala Phe Pro Leu Thr Ser Asn Gly Pro Val Cys Cys Pro Pro
1060 1065 1070

Arg Ser Thr Ser Asn Gly Thr Leu Gly Asp Pro His Phe Phe Ser Tyr
1075 1080 1085

Ser Ile Asp Val Gly Ala Leu Asp Leu Gln Ala Asn Pro Gly Ile Glu
1090 1095 1100

Phe Gly Leu Arg Ile Val Asn Pro Thr Gly Met Ala Arg Val Ser Asn
1105 1110 1115 1120

Leu Glu Ile Arg Glu Asp Arg Pro Leu Ala Ala Asn Glu Ile Arg Gln
1125 1130 1135

Val Gln Arg Val Ala Arg Asn Trp Arg Thr Glu Tyr Glu Lys Glu Arg
1140 1145 1150

Ala Glu Val Thr Ser Leu Ile Gln Pro Val Ile Asn Arg Ile Asn Gly
1155 1160 1165

Leu Tyr Glu Asn Gly Asn Trp Asn Gly Ser Ile Arg Ser Asp Ile Ser
1170 1175 1180

Tyr Gln Asn Ile Asp Ala Ile Val Leu Pro Thr Leu Pro Lys Leu Arg
1185 1190 1195 1200

-continued

```
His Trp Phe Met Ser Asp Arg Phe Ser Glu Gln Gly Asp Ile Met Ala
                1205                1210                1215

Lys Phe Gln Gly Ala Leu Asn Arg Ala Tyr Ala Gln Leu Glu Gln Ser
            1220                1225                1230

Thr Leu Leu His Asn Gly His Phe Thr Lys Asp Ala Ala Asn Trp Thr
        1235                1240                1245

Ile Glu Gly Asp Ala His Gln Ile Thr Leu Glu Asp Gly Arg Arg Val
    1250                1255                1260

Leu Arg Leu Pro Asp Trp Ser Ser Ser Val Ser Gln Met Ile Glu Ile
1265                1270                1275                1280

Glu Asn Phe Asn Pro Asp Lys Glu Tyr Asn Leu Val Phe His Gly Gln
                1285                1290                1295

Gly Glu Gly Thr Val Thr Leu Glu His Gly Glu Glu Thr Lys Tyr Ile
            1300                1305                1310

Glu Thr His Thr His His Phe Ala Asn Phe Thr Thr Ser Gln Arg Gln
        1315                1320                1325

Gly Leu Thr Phe Glu Ser Asn Lys Val Thr Val Thr Ile Ser Ser Glu
    1330                1335                1340

Asp Gly Glu Phe Leu Val Asp Asn Ile Ala Leu Val Glu Ala Pro Leu
1345                1350                1355                1360

Pro Thr Asp Asp Gln Asn Ser Glu Gly Asn Thr Ala Ser Ser Thr Asn
                1365                1370                1375

Ser Asp Thr Ser Met Asn Asn Asn Gln
            1380                1385
```

( 2 ) INFORMATION FOR SEQ ID NO:3:

( i ) SEQUENCE CHARACTERISTICS:
( A ) LENGTH: 3867 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: PS17
( C ) INDIVIDUAL ISOLATE: PS17b ( x i ) SEQUENCE DESCRIPTION: SEQ ID NO:3:

```
ATGGCAATTT TAAATGAATT ATATCCATCT GTACCTTATA ATGTATTGGC GTATACGCCA   60
CCCTCTTTTT TACCTGATGC GGGTACACAA GCTACACCTG CTGACTTAAC AGCTTATGAA  120
CAATTGTTGA AAAATTTAGA AAAAGGGATA AATGCTGGAA CTTATTCGAA AGCAATAGCT  180
GATGTACTTA AAGGTATTTT TATAGATGAT ACAATAAATT ATCAAACATA TGTAAATATT  240
GGTTTAAGTT TAATTACATT AGCTGTACCG GAAATTGGTA TTTTTACACC TTTCATCGGT  300
TTGTTTTTTG CTGCATTGAA TAAACATGAT GCTCCACCTC CTCCTAATGC AAAAGATATA  360
TTTGAGGCTA TGAAACCAGC GATTCAAGAG ATGATTGATA GAACTTTAAC TGCGGATGAG  420
CAAACATTTT TAAATGGGGA AATAAGTGGT TTACAAAATT TAGCAGCAAG ATACCAGTCT  480
ACAATGGATG ATATTCAAAG CCATGGAGGA TTTAATAAGG TAGATTCTGG ATTAATTAAA  540
AAGTTTACAG ATGAGGTACT ATCTTTAAAT AGTTTTTATA CAGATCGTTT ACCTGTATTT  600
ATTACAGATA ATACAGCGGA TCGAACTTTG TTAGGTCTTC CTTATTATGC TATACTTGCG  660
AGCATGCATC TTATGTTATT AAGAGATATC ATTACTAAGG GTCCGACATG GGATTCTAAA  720
```

-continued

ATTAATTTCA CACCAGATGC AATTGATTCC TTTAAAACCG ATATTAAAAA TAATATAAAG 780
CTTTACTCTA AAACTATTTA TGACGTATTT CAGAAGGGAC TTGCTTCATA CGGAACGCCT 840
TCTGATTTAG AGTCCTTTGC AAAAAAACAA AAATATATTG AAATTATGAC AACACATTGT 900
TTAGATTTTG CAAGATTGTT TCCTACTTTT GATCCAGATC TTTATCCAAC AGGATCAGGT 960
GATATAAGTT TACAAAAAAC ACGTAGAATT CTTTCTCCTT TTATCCCTAT ACGTACTGCA 1020
GATGGGTTAA CATTAAATAA TACTTCAATT GATACTTCAA ATTGGCCTAA TTATGAAAAT 1080
GGGAATGGCG CGTTTCCAAA CCCAAAAGAA AGAATATTAA AACAATTCAA ACTGTATCCT 1140
AGTTGGAGAG CGGCACAGTA CGGTGGGCTT TTACAACCTT ATTTATGGGC AATAGAAGTC 1200
CAAGATTCTG TAGAGACTCG TTTGTATGGG CAGCTTCCAG CTGTAGATCC ACAGGCAGGG 1260
CCTAATTATG TTTCCATAGA TTCTTCTAAT CCAATCATAC AAATAAATAT GGATACTTGG 1320
AAAACACCAC CACAAGGTGC GAGTGGGTGG AATACAAATT TAATGAGAGG AAGTGTAAGC 1380
GGGTTAAGTT TTTTACAACG AGATGGTACG AGACTTAGTG CTGGTATGGG TGGTGGTTTT 1440
GCTGATACAA TATATAGTCT CCCTGCAACT CATTATCTTT CTTATCTCTA TGGAACTCCT 1500
TATCAAACTT CTGATAACTA TTCTGGTCAC GTTGGTGCAT TGGTAGGTGT GAGTACGCCT 1560
CAAGAGGCTA CTCTTCCTAA TATTATAGGT CAACCAGATG AACAGGGAAA TGTATCTACA 1620
ATGGGATTTC CGTTTGAAAA AGCTTCTTAT GGAGGTACAG TTGTTAAAGA ATGGTTAAAT 1680
GGTGCGAATG CGATGAAGCT TTCTCCTGGG CAATCTATAG GTATTCCTAT TACAAATGTA 1740
ACAAGTGGAG AATATCAAAT TCGTTGTCGT TATGCAAGTA ATGATAATAC TAACGTTTTC 1800
TTTAATGTAG ATACTGGTGG AGCAAATCCA ATTTTCCAAC AGATAAACTT TGCATCTACT 1860
GTAGATAATA ATACGGGAGT ACAAGGAGCA AATGGTGTCT ATGTAGTCAA ATCTATTGCT 1920
ACAACTGATA ATTCTTTTAC AGTAAAAATT CCTGCGAAGA CGATTAATGT TCATTTAACC 1980
AACCAAGGTT CTTCTGATGT CTTTTTAGAT CGTATTGAGT TTGTTCCAAT TCTAGAATCA 2040
AATACTGTAA CTATATTCAA CAATTCATAT ACTACAGGTT CAGCAAATCT TATACCAGCA 2100
ATAGCTCCTC TTTGGAGTAC TAGTTCAGAT AAAGCCCTTA CAGGTTCTAT GTCAATAACA 2160
GGTCGAACTA CCCCTAACAG TGATGATGCT TTGCTTCGAT TTTTTAAAAC TAATTATGAT 2220
ACACAAACCA TTCCTATTCC GGGTTCCGGA AAAGATTTTA CAAATACTCT AGAAATACAA 2280
GACATAGTTT CTATTGATAT TTTTGTCGGA TCTGGTCTAC ATGGATCCGA TGGATCTATA 2340
AAATTAGATT TTACCAATAA TAATAGTGGT AGTGGTGGCT CTCCAAAGAG TTTCACCGAG 2400
CAAAATGATT TAGAGAATAT CACAACACAA GTGAATGCTC TATTCACATC TAATACACAA 2460
GATGCACTTG CAACAGATGT GAGTGATCAT GATATTGAAG AAGTGGTTCT AAAAGTAGAT 2520
GCATTATCTG ATGAAGTGTT TGGAAAAGAG AAAAAAACAT TGCGTAAATT TGTAAATCAA 2580
GCGAAGCGCT TAAGCAAGGC GCGTAATCTC CTGGTAGGAG GCAATTTTGA TAACTTGGAT 2640
GCTTGGTATA GAGGAAGAAA TGTAGTAAAC GTATCTAATC ACGAACTGTT GAAGAGTGAT 2700
CATGTATTAT TACCACCACC AGGATTGTCT CCATCTTATA TTTTCCAAAA AGTGGAGGAA 2760
TCTAAATTAA AACGAAATAC ACGTTATACG GTTTCTGGAT TTATTGCGCA TGCAACAGAT 2820
TTAGAAATTG TGGTTTCTCG TTATGGGCAA GAAATAAAGA AAGTGGTGCA AGTTCCTTAT 2880
GGAGAAGCAT TCCCATTAAC ATCAAGTGGA CCAGTTTGTT GTATCCCACA TTCTACAAGT 2940
AATGGAACTT TAGGCAATCC ACATTTCTTT AGTTACAGTA TTGATGTAGG TGCATTAGAT 3000
GTAGACACAA ACCCTGGTAT TGAATTCGGT CTTCGTATTG TAAATCCAAC TGGAATGGCA 3060
CGCGTAAGCA ATTTGGAAAT TCGTGAAGAT CGTCCATTAG CAGCAAATGA AATACGACAA 3120
GTACAACGTG TCGCAAGAAA TTGGAGAACC GAGTATGAGA AAGAACGTGC GGAAGTAACA 3180

-continued

AGTTTAATTC AACCTGTTAT CAATCGAATC AATGGATTGT ATGACAATGG AAATTGGAAC 3240
GGTTCTATTC GTTCAGATAT TTCGTATCAG AATATAGACG CGATTGTATT ACCAACGTTA 3300
CCAAAGTTAC GCCATTGGTT TATGTCAGAT AGATTTAGTG AACAAGGAGA TATCATGGCT 3360
AAATTCCAAG GTGCATTAAA TCGTGCGTAT GCACAACTGG AACAAAATAC GCTTCTGCAT 3420
AATGGTCATT TTACAAAAGA TGCAGCCAAT TGGACGGTAG AAGGCGATGC ACATCAGGTA 3480
GTATTAGAAG ATGGTAAACG TGTATTACGA TTGCCAGATT GGTCTTCGAG TGTGTCTCAA 3540
ACGATTGAAA TCGAGAATTT TGATCCAGAT AAAGAATATC AATTAGTATT TCATGGGCAA 3600
GGAGAAGGAA CGGTTACGTT GGAGCATGGA GAAGAAACAA AATATATAGA AACGCATACA 3660
CATCATTTTG CGAATTTTAC AACTTCTCAA CGTCAAGGAC TCACGTTTGA ATCAAATAAA 3720
GTGACAGTGA CCATTTCTTC AGAAGATGGA GAATTCTTAG TGGATAATAT TGCGCTTGTG 3780
GAAGCTCCTC TTCCTACAGA TGACCAAAAT TCTGAGGGAA ATACGGCTTC CAGTACGAAT 3840
AGCGATACAA GTATGAACAA CAATCAA 3867

( 2 ) INFORMATION FOR SEQ ID NO:4:

( i ) SEQUENCE CHARACTERISTICS:
( A ) LENGTH: 1289 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: PS17
( C ) INDIVIDUAL ISOLATE: PS17b ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Ala | Ile | Leu | Asn | Glu | Leu | Tyr | Pro | Ser | Val | Pro | Tyr | Asn | Val | Leu |
| 1 | | | | 5 | | | | | 10 | | | | | 15 | |
| Ala | Tyr | Thr | Pro | Pro | Ser | Phe | Leu | Pro | Asp | Ala | Gly | Thr | Gln | Ala | Thr |
| | | | 20 | | | | | 25 | | | | | 30 | | |
| Pro | Ala | Asp | Leu | Thr | Ala | Tyr | Glu | Gln | Leu | Leu | Lys | Asn | Leu | Glu | Lys |
| | | 35 | | | | | 40 | | | | | 45 | | | |
| Gly | Ile | Asn | Ala | Gly | Thr | Tyr | Ser | Lys | Ala | Ile | Ala | Asp | Val | Leu | Lys |
| | 50 | | | | | 55 | | | | | 60 | | | | |
| Gly | Ile | Phe | Ile | Asp | Asp | Thr | Ile | Asn | Tyr | Gln | Thr | Tyr | Val | Asn | Ile |
| 65 | | | | | 70 | | | | | 75 | | | | | 80 |
| Gly | Leu | Ser | Leu | Ile | Thr | Leu | Ala | Val | Pro | Glu | Ile | Gly | Ile | Phe | Thr |
| | | | | 85 | | | | | 90 | | | | | 95 | |
| Pro | Phe | Ile | Gly | Leu | Phe | Phe | Ala | Ala | Leu | Asn | Lys | His | Asp | Ala | Pro |
| | | | 100 | | | | | 105 | | | | | 110 | | |
| Pro | Pro | Pro | Asn | Ala | Lys | Asp | Ile | Phe | Glu | Ala | Met | Lys | Pro | Ala | Ile |
| | | 115 | | | | | 120 | | | | | 125 | | | |
| Gln | Glu | Met | Ile | Asp | Arg | Thr | Leu | Thr | Ala | Asp | Glu | Gln | Thr | Phe | Leu |
| | 130 | | | | | 135 | | | | | 140 | | | | |
| Asn | Gly | Glu | Ile | Ser | Gly | Leu | Gln | Asn | Leu | Ala | Ala | Arg | Tyr | Gln | Ser |
| 145 | | | | | 150 | | | | | 155 | | | | | 160 |
| Thr | Met | Asp | Asp | Ile | Gln | Ser | His | Gly | Gly | Phe | Asn | Lys | Val | Asp | Ser |
| | | | | 165 | | | | | 170 | | | | | 175 | |
| Gly | Leu | Ile | Lys | Lys | Phe | Thr | Asp | Glu | Val | Leu | Ser | Leu | Asn | Ser | Phe |
| | | | 180 | | | | | 185 | | | | | 190 | | |

-continued

| | | | | | | | | | | | | | | | |
|---|---|---|---|---|---|---|---|---|---|---|---|---|---|---|---|
| Tyr | Thr | Asp | Arg | Leu | Pro | Val | Phe | Ile | Thr | Asp | Asn | Thr | Ala | Asp | Arg |
| | | 195 | | | | | 200 | | | | | 205 | | | |
| Thr | Leu | Leu | Gly | Leu | Pro | Tyr | Tyr | Ala | Ile | Leu | Ala | Ser | Met | His | Leu |
| | 210 | | | | | 215 | | | | | 220 | | | | |
| Met | Leu | Leu | Arg | Asp | Ile | Ile | Thr | Lys | Gly | Pro | Thr | Trp | Asp | Ser | Lys |
| 225 | | | | | 230 | | | | | 235 | | | | | 240 |
| Ile | Asn | Phe | Thr | Pro | Asp | Ala | Ile | Asp | Ser | Phe | Lys | Thr | Asp | Ile | Lys |
| | | | | 245 | | | | | 250 | | | | | 255 | |
| Asn | Asn | Ile | Lys | Leu | Tyr | Ser | Lys | Thr | Ile | Tyr | Asp | Val | Phe | Gln | Lys |
| | | | 260 | | | | | 265 | | | | | 270 | | |
| Gly | Leu | Ala | Ser | Tyr | Gly | Thr | Pro | Ser | Asp | Leu | Glu | Ser | Phe | Ala | Lys |
| | | 275 | | | | | 280 | | | | | 285 | | | |
| Lys | Gln | Lys | Tyr | Ile | Glu | Ile | Met | Thr | Thr | His | Cys | Leu | Asp | Phe | Ala |
| | 290 | | | | | 295 | | | | | 300 | | | | |
| Arg | Leu | Phe | Pro | Thr | Phe | Asp | Pro | Asp | Leu | Tyr | Pro | Thr | Gly | Ser | Gly |
| 305 | | | | | 310 | | | | | 315 | | | | | 320 |
| Asp | Ile | Ser | Leu | Gln | Lys | Thr | Arg | Arg | Ile | Leu | Ser | Pro | Phe | Ile | Pro |
| | | | | 325 | | | | | 330 | | | | | 335 | |
| Ile | Arg | Thr | Ala | Asp | Gly | Leu | Thr | Leu | Asn | Asn | Thr | Ser | Ile | Asp | Thr |
| | | | 340 | | | | | 345 | | | | | 350 | | |
| Ser | Asn | Trp | Pro | Asn | Tyr | Glu | Asn | Gly | Asn | Gly | Ala | Phe | Pro | Asn | Pro |
| | | 355 | | | | | 360 | | | | | 365 | | | |
| Lys | Glu | Arg | Ile | Leu | Lys | Gln | Phe | Lys | Leu | Tyr | Pro | Ser | Trp | Arg | Ala |
| | 370 | | | | | 375 | | | | | 380 | | | | |
| Ala | Gln | Tyr | Gly | Gly | Leu | Leu | Gln | Pro | Tyr | Leu | Trp | Ala | Ile | Glu | Val |
| 385 | | | | | 390 | | | | | 395 | | | | | 400 |
| Gln | Asp | Ser | Val | Glu | Thr | Arg | Leu | Tyr | Gly | Gln | Leu | Pro | Ala | Val | Asp |
| | | | | 405 | | | | | 410 | | | | | 415 | |
| Pro | Gln | Ala | Gly | Pro | Asn | Tyr | Val | Ser | Ile | Asp | Ser | Ser | Asn | Pro | Ile |
| | | | 420 | | | | | 425 | | | | | 430 | | |
| Ile | Gln | Ile | Asn | Met | Asp | Thr | Trp | Lys | Thr | Pro | Pro | Gln | Gly | Ala | Ser |
| | | 435 | | | | | 440 | | | | | 445 | | | |
| Gly | Trp | Asn | Thr | Asn | Leu | Met | Arg | Gly | Ser | Val | Ser | Gly | Leu | Ser | Phe |
| | 450 | | | | | 455 | | | | | 460 | | | | |
| Leu | Gln | Arg | Asp | Gly | Thr | Arg | Leu | Ser | Ala | Gly | Met | Gly | Gly | Gly | Phe |
| 465 | | | | | 470 | | | | | 475 | | | | | 480 |
| Ala | Asp | Thr | Ile | Tyr | Ser | Leu | Pro | Ala | Thr | His | Tyr | Leu | Ser | Tyr | Leu |
| | | | | 485 | | | | | 490 | | | | | 495 | |
| Tyr | Gly | Thr | Pro | Tyr | Gln | Thr | Ser | Asp | Asn | Tyr | Ser | Gly | His | Val | Gly |
| | | | 500 | | | | | 505 | | | | | 510 | | |
| Ala | Leu | Val | Gly | Val | Ser | Thr | Pro | Gln | Glu | Ala | Thr | Leu | Pro | Asn | Ile |
| | | 515 | | | | | 520 | | | | | 525 | | | |
| Ile | Gly | Gln | Pro | Asp | Glu | Gln | Gly | Asn | Val | Ser | Thr | Met | Gly | Phe | Pro |
| | 530 | | | | | 535 | | | | | 540 | | | | |
| Phe | Glu | Lys | Ala | Ser | Tyr | Gly | Gly | Thr | Val | Val | Lys | Glu | Trp | Leu | Asn |
| 545 | | | | | 550 | | | | | 555 | | | | | 560 |
| Gly | Ala | Asn | Ala | Met | Lys | Leu | Ser | Pro | Gly | Gln | Ser | Ile | Gly | Ile | Pro |
| | | | | 565 | | | | | 570 | | | | | 575 | |
| Ile | Thr | Asn | Val | Thr | Ser | Gly | Glu | Tyr | Gln | Ile | Arg | Cys | Arg | Tyr | Ala |
| | | | 580 | | | | | 585 | | | | | 590 | | |
| Ser | Asn | Asp | Asn | Thr | Asn | Val | Phe | Phe | Asn | Val | Asp | Thr | Gly | Gly | Ala |
| | | 595 | | | | | 600 | | | | | 605 | | | |
| Asn | Pro | Ile | Phe | Gln | Gln | Ile | Asn | Phe | Ala | Ser | Thr | Val | Asp | Asn | Asn |
| | 610 | | | | | 615 | | | | | 620 | | | | |
| Thr | Gly | Val | Gln | Gly | Ala | Asn | Gly | Val | Tyr | Val | Val | Lys | Ser | Ile | Ala |

-continued

```
625                 630                 635                 640

Thr Thr Asp Asn Ser Phe Thr Val Lys Ile Pro Ala Lys Thr Ile Asn
                645                 650                 655

Val His Leu Thr Asn Gln Gly Ser Ser Asp Val Phe Leu Asp Arg Ile
            660                 665                 670

Glu Phe Val Pro Ile Leu Glu Ser Asn Thr Val Thr Ile Phe Asn Asn
        675                 680                 685

Ser Tyr Thr Thr Gly Ser Ala Asn Leu Ile Pro Ala Ile Ala Pro Leu
    690                 695                 700

Trp Ser Thr Ser Ser Asp Lys Ala Leu Thr Gly Ser Met Ser Ile Thr
705                 710                 715                 720

Gly Arg Thr Thr Pro Asn Ser Asp Asp Ala Leu Leu Arg Phe Phe Lys
                725                 730                 735

Thr Asn Tyr Asp Thr Gln Thr Ile Pro Ile Pro Gly Ser Gly Lys Asp
            740                 745                 750

Phe Thr Asn Thr Leu Glu Ile Gln Asp Ile Val Ser Ile Asp Ile Phe
        755                 760                 765

Val Gly Ser Gly Leu His Gly Ser Asp Gly Ser Ile Lys Leu Asp Phe
    770                 775                 780

Thr Asn Asn Asn Ser Gly Ser Gly Gly Ser Pro Lys Ser Phe Thr Glu
785                 790                 795                 800

Gln Asn Asp Leu Glu Asn Ile Thr Thr Gln Val Asn Ala Leu Phe Thr
                805                 810                 815

Ser Asn Thr Gln Asp Ala Leu Ala Thr Asp Val Ser Asp His Asp Ile
            820                 825                 830

Glu Glu Val Val Leu Lys Val Asp Ala Leu Ser Asp Glu Val Phe Gly
        835                 840                 845

Lys Glu Lys Lys Thr Leu Arg Lys Phe Val Asn Gln Ala Lys Arg Leu
    850                 855                 860

Ser Lys Ala Arg Asn Leu Leu Val Gly Gly Asn Phe Asp Asn Leu Asp
865                 870                 875                 880

Ala Trp Tyr Arg Gly Arg Asn Val Val Asn Val Ser Asn His Glu Leu
                885                 890                 895

Leu Lys Ser Asp His Val Leu Leu Pro Pro Pro Gly Leu Ser Pro Ser
            900                 905                 910

Tyr Ile Phe Gln Lys Val Glu Glu Ser Lys Leu Lys Arg Asn Thr Arg
        915                 920                 925

Tyr Thr Val Ser Gly Phe Ile Ala His Ala Thr Asp Leu Glu Ile Val
    930                 935                 940

Val Ser Arg Tyr Gly Gln Glu Ile Lys Lys Val Val Gln Val Pro Tyr
945                 950                 955                 960

Gly Glu Ala Phe Pro Leu Thr Ser Ser Gly Pro Val Cys Cys Ile Pro
                965                 970                 975

His Ser Thr Ser Asn Gly Thr Leu Gly Asn Pro His Phe Phe Ser Tyr
            980                 985                 990

Ser Ile Asp Val Gly Ala Leu Asp Val Asp Thr Asn Pro Gly Ile Glu
        995                 1000                1005

Phe Gly Leu Arg Ile Val Asn Pro Thr Gly Met Ala Arg Val Ser Asn
    1010                1015                1020

Leu Glu Ile Arg Glu Asp Arg Pro Leu Ala Ala Asn Glu Ile Arg Gln
1025                1030                1035                1040

Val Gln Arg Val Ala Arg Asn Trp Arg Thr Glu Tyr Glu Lys Glu Arg
                1045                1050                1055

Ala Glu Val Thr Ser Leu Ile Gln Pro Val Ile Asn Arg Ile Asn Gly
            1060                1065                1070
```

-continued

Leu Tyr Asp Asn Gly Asn Trp Asn Gly Ser Ile Arg Ser Asp Ile Ser
1075 1080 1085

Tyr Gln Asn Ile Asp Ala Ile Val Leu Pro Thr Leu Pro Lys Leu Arg
1090 1095 1100

His Trp Phe Met Ser Asp Arg Phe Ser Glu Gln Gly Asp Ile Met Ala
1105 1110 1115 1120

Lys Phe Gln Gly Ala Leu Asn Arg Ala Tyr Ala Gln Leu Glu Gln Asn
1125 1130 1135

Thr Leu Leu His Asn Gly His Phe Thr Lys Asp Ala Ala Asn Trp Thr
1140 1145 1150

Val Glu Gly Asp Ala His Gln Val Val Leu Glu Asp Gly Lys Arg Val
1155 1160 1165

Leu Arg Leu Pro Asp Trp Ser Ser Ser Val Ser Gln Thr Ile Glu Ile
1170 1175 1180

Glu Asn Phe Asp Pro Asp Lys Glu Tyr Gln Leu Val Phe His Gly Gln
1185 1190 1195 1200

Gly Glu Gly Thr Val Thr Leu Glu His Gly Glu Glu Thr Lys Tyr Ile
1205 1210 1215

Glu Thr His Thr His His Phe Ala Asn Phe Thr Thr Ser Gln Arg Gln
1220 1225 1230

Gly Leu Thr Phe Glu Ser Asn Lys Val Thr Val Thr Ile Ser Ser Glu
1235 1240 1245

Asp Gly Glu Phe Leu Val Asp Asn Ile Ala Leu Val Glu Ala Pro Leu
1250 1255 1260

Pro Thr Asp Asp Gln Asn Ser Glu Gly Asn Thr Ala Ser Ser Thr Asn
1265 1270 1275 1280

Ser Asp Thr Ser Met Asn Asn Asn Gln
1285

*BACILLUS THURINGIENSIS* ISOLATES FOR CONTROLLING ACARIDES

CROSS-REFERENCE TO RELATED APPLICATIONS

This is a continuation-in-pan of co-pending application Ser. No. 07/768,141, filed Sep. 30, 1991, which is a continuation-in-part of application Ser. No. 07/759,248, filed Sep. 13, 1991, now abandoned.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The B.t. microbes produce a variety of toms. A mouse-lethal ct-exotoxin is produced by certain isolates of this species, as well as two types of hemolysins, a nucleotide $\beta$-exotoxin and $\delta$-endotoxins. Delta-endotoxins are derived from the parasporal crystalline protein inclusions and are highly toxic to pests and specific in their toxic activity. The B.t. toxins have been commercially exploited for their use in pest control. Certain B.t. endotoxin genes have been isolated and sequenced, and recombinant DNA-based B.t. products have been produced and approved for use. In addition, with the use of genetic engineering techniques, new approaches for delivering B.t. endotoxins to agricultural environments are under development, including the use of plants genetically engineered with endotoxin genes for insect resistance and the use of stabilized intact microbial cells as B.t. endotoxin delivery vehicles (Gaertner, F.H., L. Kim [1988]TIBTECH 6:S4–S7).

Until the last 10 years, commercial use of B.t. pesticides has been largely restricted to a narrow range of lepidopteran (caterpillar) pests. Preparations of the spores and crystals of *B. thudngiensis* subsp. kurstaki have been used for many years as commercial insecticides for lepidopteran pests. For example, *B. thuringiensis* var. *kurstaki* HD-1 produces a delta-endotoxin which is toxic to the larvae of a number of lepidopteran insects.

In recent years, however, investigators have discovered B.t. pesticides with specificities for a much broader range of pests. For example, other species of B.t., namely israelensis and san diego (a.k.a.B.t. tenebdonis, a.k.a. M-7), have been used commercially to control insects of the orders Diptera and Coleoptera, respectively (Gaertner, F.H. [1989]"Cellular Delivery Systems for Insecticidal Proteins: Living and Non-Living Microorganisms," in *Controlled Delivery of Crop Protection Agents,* R.M. Wilkins, ed., Taylor and Francis, New York and London, 1990, pp. 245–255). See also Couch, T.L. (1980) "Mosquito Pathogenicity of *Bacillus thudngiensis* var. *israelensis,*" *Developments in Industrial Microbiology* 22:61–76; Beegle, C.C., (1978) "Use of Entomogenous Bacteria in Agroecosystems," *Developments in Industrial Microbiology* 20:97–104. Krieg, A., A.M. Huger, G.A. Langenbruch, W. Sctmetter (1983) Z. ang. Ent. 96:500-508, describe a B.t. isolate named *Bacillus thuringiensis* var. *tenebrionis,* which is reportedly active against two beetles in the order Coleoptera. These are the Colorado potato beetle, *Leptinotarsa decemlineata,* and *Agelastica alni.*

There have been published reports concerning the use of *Bacillus thudngiensis* preparations for the control of acarid pests or mites. These publications are as follow:

Royalty, R.N., F.R. HaH, R.A.J. Taylor (1990) "Effects of thuringiensin on *Tetranychus urticae* (Acari: Tetranychidae) mortality, fecundity, and feeding," *J. Econ. Entomot* 83:792–798.

Neal, J.W., R.K. Lindquist, K.M. Gott, M.L. Casey (1987) "Activity of the themostable beta-exotoxin of *Bacillus thudngiensis* Berliner on *Tetranychus urticae* and *Tetranychus cinnabarinus,*"*J. Agric. Entomol.* 4:33–40.

Vlayen, P., G. Impe, R. Van Semaille (1978) "Effect of a commercial preparation of *Bacillus thuringiensis* on the spider mite *Tetranychus urticae* Koch. (Acari: Tetranychidae)," *Mededelingen* 43:471–479.

In the above published studies, the active ingredient in the B.t. preparations was $\beta$-exotoxin (also called thuringiensin).

The major focus for commercial use of B.t. toxins is on the $\delta$-endotoxins from the parasporal crystalline protein inclusions. Recently, new subspecies of B.t. have been identified, and genes responsible for active $\delta$-endotoxin proteins have been isolated (Höfte, H., H.R. Whiteley [1989]*Microbiological Reviews* 52(2):242–255). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J.S., J. Payne, L. Kim [1992]*Bio/Technology* 10:271–275).

The cloning and expression of a *B.t.* crystal protein gene in *Escherichia coli* has been described in the published literature (Schnepf, H.E., H.R. Whitely [1981]*Proc. Natl. Acad. Sci. USA* 78:2893–2897). U.S. Pat. No. 4,448,885 and U.S. Pat. No. 4,467,036 both disclose the expression of *B.t.* crystal proteins in *E. coli.* U.S. Pat. Nos. 4,797,276 and 4,853,331 disclose *B. thuringiensis* strain *san diego* (a.k.a.B.t. tenebrionis, a.k.a. M-7) which can be used to control coleopteran pests in various environments. U.S. Pat. No. 4,849,217 discloses isolates of B.t. which have activity against a coleopteran pests, the alfalfa weevil, while U.S. Pat. No. 4,948,734 discloses certain isolates of B.t. which have activity against nematodes. U.S. Pat. No. 5,093,120 discloses the use of these B.t. isolates to control nematode infections in animals and plants. Many other patents have issued for new B.t. isolates and new uses of B.t. isolates. The discovery of new B.t. isolates and new uses of known B.t. isolates remains an empirical, unpredictable art.

BRIEF SUMMARY OF THE INVENTION

The subject invention concerns *Bacillus thuringiensis* isolates which have acaridicidal properties. Unlike published reports of the use of B.t. $\beta$-exotoxins to control mites, the subject invention isolates express $\delta$-endotoxins which control mites. The use of $\delta$-endotoxins is highly advantageous in view of the known general toxicity of $\beta$-exotoxins to humans and animals.

More specifically, the subject invention concerns *Bacillus thuringiensis* isolates designated B.t. PS45B1, B.t. PS24J, B.t. PS94R3, B.t. PS17, B.t. PS62B1 and B.t. PS74G1.

The B.t. isolates of the subject invention are toxic to the two spotted spider mite, *Tetranychus urticae* and the house dust mite, *Dermatophagoides pteronyssinus.* Thus, these isolates can be used to control these mites. Further, the δ-endotoxins from these B.t. isolates can be isolated by standard procedures, e.g. ion exchange, and formulated by standard procedures to control these mites. These B.t. isolates can also be used against non-phytophagous mites such as acarid pests of livestock, fowl and stored products. Still further, the gene(s) from the B.t. isolates of the invention which encode the acaridicidal toxin can be cloned from the isolates and then used to transform other hosts, e.g., prokaryotic, eukaryotic or plants, which transformed host can be used to control mites, or, in the case of transgenie plants, be resistant to mites.

BRIEF DESCRIPTION OF THE SEQUENCES

Figure 1:
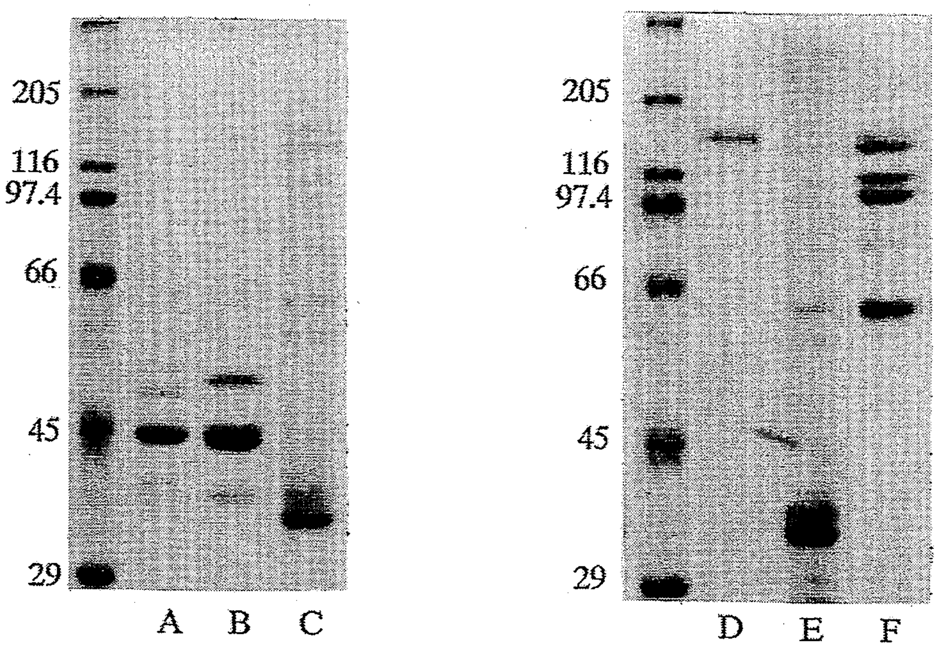
FIG. 1 is a photograph of a 12% SDS polyacrylamide gel showing alkali-soluble proteins of the isolates of the invention.

SEQ ID NO. 1 discloses the DNA of PS17a.

SEQ ID NO. 2 discloses the amino acid sequence of the toxin encoded by PS17a.

SEQ ID NO. 3 discloses the DNA of PS17b.

SEQ ID NO. 4 discloses the amino acid sequence of the toxin encoded by PS17b.

DETAILED DISCLOSURE OF THE INVENTION

A summary of the characteristics of the *B. thuringiensis* microbes of the subject invention is shown in Table 1.

TABLE 1

A comparison of the acarid-active strains of the invention

| Strain | Crystal Type | Approx. Mol. Wt. of Proteins (kDa) |
|---|---|---|
| *B. thuringiensis* PS24J | Long | 51, 48, 43 |
| *B. thuringiensis* PS94R3 | Long | 50, 43, 42 |
| *B. thuringiensis* PS45B1 | Multiple | 150, 135, 35 |
| *B. thuringiensis* PS17 | Long | 155, 145, 128 |
| *B. thuringiensis* PS62B1 | Attached Multiple | 35 |
| *B. thuringiensis* PS74G1 | Amorphic | 148, 112, 104, 61 |

Additionally, the isolates have the following common characteristics:

Colony morphology—large colony, dull surface, typical B.t.

Vegetative cell morphology—typical B.t.

The B.t. isolates of the invention, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains. The novel B.t. isolates, and mutants thereof, can be used to control target pests.

The cultures of the subject invention were deposited in the Agricultural Research Service Patent Culture Collection (NRRL), Northern Regional Research Center, 1815 North University Street, Peoria, Ill., 61604 USA.

| Culture | Accession No. | Deposit Date |
|---|---|---|
| *B. thuringiensis* PS45B1 | NRRL B-18396 | August 16, 1988 |
| *B. thuringiensis* PS24J | NRRL B-18881 | August 30, 1991 |
| *B. thuringiensis* PS94R3 | NRRL B-18882 | August 30, 1991 |
| *B. thuringiensis* PS17 | NRRL B-18243 | July 28, 1987 |
| *B. thuringiensis* PS62B1 | NRRL B-18398 | August 16, 1988 |
| *B. thuringiensis* PS74G1 | NRRL B-18397 | August 16, 1988 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing a culture. The depositor acknowledges the duty to replace a deposit should the depository be unable to furnish a sample when requested, due to the condition of the deposit(s). All restrictions on the availability to the public of the subject culture deposits will be irrevocably removed upon the granting of a patent disclosing them.

Genes and toms. The genes and toxins according to the subject invention include fragments of the genes and toxin proteins, which retain the characteristic pesticidal activity of the toxins specifically exemplified herein.

It should be apparent to a person skilled in this art that genes coding for acarid-active toxins can be identified and obtained through several means. The specific genes exemplified herein may be obtained from the isolates deposited at a culture depository as described above. These genes, or portions or variants thereof, may also be constructed synthetically, for example, by use of a gene machine. As used herein, the terms "variants" or "variations" of genes refer to nucleotides which code for the same toxins or which code for equivalent toxins having acafid activity. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Variant toxins and/or genes encoding these variant toxins can also be located from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are nucleotide sequences having a detectable label. As is well known in the art, ff the probe molecule and nucleic acid sample hybridize by forming a strong bond between the two molecules, it can be reasonably assumed that the probe and sample have substantial homology. The probe's detectable label provides a means for determining in a known manner whether hybridization has occurred. Such a probe analysis provides a rapid method for identifying tom-encoding genes of the subject invention. The nucleotide segments which are used as probes according to the invention can be synthesized by use of DNA synthesizers using standard procedures.

These fragments and mutations, which retain the pesticidal activity of the exemplified toms, would be within the scope of the subject invention. Also, because of the redundancy of the genetic code, a variety of different DNA sequences can encode the toxins disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining acarid activity are also included in this definition.

Toxins of the subject invention further comprises variant toxins (and nucleotide sequences coding for variant toxins). Variant toxins are toxins of the subject invention that have been treated, purified, or otherwise altered but retain the same biological activity against acarids. In this regard, certain amino acid substitutions within the amino acid sequence of the toxin are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudornonas, the microbes can be applied to the situs of mites where they will proliferate and be ingested by the pest. The result is a control of this pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said microbial host is applied to the environment in a living state, it is essential that certain host microbes be used. Microorganism hosts are selected which are known to occupy the soil. These microorganisms are selected so as to be capable of successfully competing in the soft with the wild-type microorganisms. It is also important that they provide for stable maintenance and expression of the gene expressing the polypeptide pesticide, and, desirably, provide for improved protection of the pesticide from environmental degradation and inactivation.

A large number of microorganisms are known to inhabit the rhizosphere (the soil surrounding plant roots). These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agobacterium , Acetobacter, Lactobacillus, Arthrobacter, Azotobacter, Leuconostoc, Alcaligenes and Clostridium; fungi, particularly yeast, e.g., genera Saccharomyces, Cryptococcus, Kluyveromyces, Sporobolomyces, Rhodotorula, and Aureobasidiurn; microalgae, e.g., families Cyanophyceae, Prochlorophyceae, Rhodophyceae, Dinophyceae, Chrysophyceae, Prymnesiophyceae, Xanthophyceae, Raphidophyceae, Bacillariophyceae, Eustigrnatophyceae, Cryptophyceae, Euglenophyceae, Prasinophyceae, and Chlorophyceae. Of particular interest are such phytosphere bacterial species as *Pseudomonas syringae. Pseudomonas fluorescens, Serratia marcescens, Acetobacter xylinum, Agrobacteriurn tumefaciens, Rhodopseudomonas spheroides, Xanthomonas campestris, Rhizobiurn melioti, AIcaligenes entrophus,* and *Azotobacter vinlandii;* and phytosphere yeast species such as *Rhodotorula rubra, R. glutinis, R. marina, R. aurantiaca, Cryptococcus albidus, C. diffiuens, C. laurentii, Saccharomyces rosei, S. pretoriensis, S. cerevisiae, Sporobolomyces roseus, S. odorus, IGuyveromyces veronae,* and *Aureobasidiurn pol-*

*lulans.* Of particular interest are the pigmented microorganisms.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, B.t. or recombinant cells expressing a B.t. toxin can be treated to prolong the toxin activity and stabilize the cell for application to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the prolfferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., *Animal Tissue Techniques,* W.H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the B.t. isolates, or recombinant microbes comprising the gene(s) obtainable from the B.t. isolates disclosed herein, can be applied to the soil. Formulated product can also be applied as a seed-coating or root treatment or total plant treatment at later stages of the crop cycle.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$cells/mg. These formulations will be administered at about 50 mg (liquid or dry) to 1 kg or more per hectare.

The formulations can be applied to the environment of the acarid, e.g., soil, by spraying, dusting, sprinkling, or the like.

Mutants. Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1—CULTURING OF THE B.T. ISOLATES

A subculture of the B.t. isolates, or mutants thereof, can be used to inoculate the following medium, a peptone, glucose, salts medium.

| | |
|---|---|
| Bacto Peptone | 7.5 g/l |
| Glucose | 1.0 g/l |
| $K_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrigugation.

EXAMPLE 2—ACTIVITY OF B.T. ISOLATES AGAINST MITES

All *B. thuringiensis* isolates of the invention were tested as spray-dried powders of fermentation broths which were concentrated by centrifugation. Pellets, which consist of water and biomass (spores, crystalline delta-endotoxins, cellular debris and growth media) were mixed with a standard carrier, preservative and surfactant. Powders, which consisted of 25% biomass, were made using a Yamato spray drier (sold by Yamato Scientific Co., Ltd. Tokyo, Japan).

All broths were tested for the presence of beta-exotoxin by a larval house fly bioassay (Campbell, D.P., D.E. Dieball, J.M. Brackett [1987]"Rapid HPLC assay for the β-exotoxin of *Bacillus thurbtgiensis,*" *J. Agric. Food Chem.* 35:156-158). Only isolates which tested free of β-exotoxin were used in the assays against mites.

*B. thuringiensis* isolates were tested using an artificial feeding assay. Spray-dried powders were prepared for testing by mixing 25 mg of powder in 5 ml of a 10% sucrose solution. This mixture was then sonicated for 8 min to produce a suspension.

Two ml of suspension was placed in a reservoir consisting of a metal ring with a Parafilm TM M film bottom. A petri dish containing approximately 30 female two-spotted spider mites (*Tetranychus urticae*) was placed on the underside of the film. Mites were allowed to feed on the sucrose solution for 24 hrs and then were transferred to 2 cm French bean leaf discs (20 mites per disc). Mortality was determined after 7 days (Table 3). Each assay was done in triplicate.

TABLE 3

Toxicity of *Bacillus thuringiensis* isolates to the two spotted spider mite, *Tetranychus urticae*

| Isolate | Percent Mortality |
|---|---|
| B.t. PS45B1 | 82 |
| B.t. PS24J | 90 |
| B.t. PS94R3 | 97 |
| B.t. PS17 | >90 |
| B.t. PS62B1 | >90 |
| B.t. PS74G1 | >90 |
| Control | 10 |

EXAMPLE 3—INSERTION OF TOXIN GENES INTO PLANTS

One aspect of the subject invention is the transformation of plants with genes encoding an acarid toxin. The transformed plants are resistant to attack by mites.

Genes encoding acarid-active toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13 mp series, pACYC184, etc. Accordingly, the sequence encoding the B.t. toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B.V., Alblasserdam, Chapter 5; Fraley et al., *Grit. Rev. Plant Sci.* 4:1–46; and An et al. (1985) EMBO J. 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacteriurn turnefaciens* or *Agobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agobacterium turnefaciens* by means of a helper plasmid (conjugation). Binary vectors can replicate themselves both in E. coli and in agrobacteria. They comprise a selection marker gene and a linker or polylinker which are framed by the right and left T-DNA border regions. They can be transformed directly into agrobacteria (Holsters et al. [1978]Mot *Gen. Genet.* 163:181–187). The agrobacterium used as host cell is to comprise a plasmid carrying a vir region. The v/r region is necessary for the transfer of the T-DNA into the plant cell. Additional T-DNA may be contained. The bacterium so transformed is used for the transformation of plant cells. Plant explants can advantageously be cultivated with *Agrobacterium turnefaciens* or *Agrobacteriurn rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electropotation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 4—CLONING OF NOVEL B.T. GENES INTO INSECT VIRUSES

A number of viruses are known to infect insects. These viruses include, for example, baculoviruses and entomopoxviruses. In one embodiment of the subject invention, lepidopteran-active genes, as described herein, can be placed with the genome of the insect virus, thus enhancing the pathogenicity of the virus. Methods for constructing insect viruses which comprise B.t. toxin genes are well known and readily practiced by those skilled in the art. These procedures are described, for example, in Merryweather et aL (Merryweather, A.T., U. Weyer, M.P.G. Harris, M. Hirst, T. Booth, R.D. Possee [1990]*J. Gen. Virol.* 71:1535–1544) and Martens et al. (Martens, J.W.M., G. Honee, D. Zuidema, J.W.M. van Lent, B. Visser, J.M. Vlak [1990]*Appl. Environmental Microbiol* 56(9):2764–2770).

EXAMPLE 5—ACTIVITY OF B.T. ISOLATES AGAINST MITES OF THE SUBORDER ACARIDIDA

The following bioassay results on the house dust mite indicate a broad spectrum of activity within the order Acari for these B.t. strains of the subject invention.

Bioassays on *Dermatophagoides pteronyssinus* were set-up using 5 replicates of 8–13 females per cage held at 22° C. and 75% relative humidity. The *Bacillus thuringiensis* spray-dried powder (30% a.i.) was incorporated into the mite's food mixture at a level of 10% by weight. Adult mortality was determined 7 days after treatment. Nymph mortality was determined 21 days after treatment (Table 4).

TABLE 4

Toxicity of *Bacillus thuringiensis* isolates to the house dust mite *Dermatophagiodes pteronysinus*

| B.t. strain | Live adults (day 7/ day 0) | % Live Adults | # Live nymphs | Live nymphs (% of control) |
|---|---|---|---|---|
| Control | 48/50 | 96 | 1577 | 100.0 |
| PS45B1 | 52/58 | 89 | 893 | 56.6 |
| PS62B1 | 50/54 | 92 | 1279 | 81.1 |
| PS74G1 | 49/53 | 92 | 1127 | 71.5 |
| PS17 | 46/48 | 96 | 897 | 56.9 |
| PS94R3 | 44/50 | 88 | 868 | 55.0 |
| PS24J | 31/45 | 69 | 626 | 39.6 |

Each of the isolates tested shows activity against the house dust mite. This activity is most pronounced against the nymphs.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A process for controlling house dust mites (*Dermatophagodes pteronyssinus*) which comprises contacting said pests with an acarid-controlling effective amount of a *Bacillus thuringiensis* isolate selected from the group consisting of B.T. OS45B1, B.t. PS24J, G.t. PS94R3, B.t. PS17, B.t. PS62B1 and B.t. PS74G1, and toxins or mutants thereof which retain the property of activity against house dust mites.

2. The process, according to claim 1, wherein said microbe is *Bacillus thuringiensis* PS45B1.

3. The process, according to claim 1, wherein said microbe is *Bacillus thuringiensis* PS24J.

4. The process, according to claim 1, wherein said microbe is *Bacillus thuringiensis* PS94R3.

5. The process, according to claim 1, wherein said microbe is *Bacillus thuringiensis* PS17.

6. The process, according to claim 1, wherein said microbe is *Bacillus thuringiensis* PS62B1.

7. The process, according to claim 1, wherein said microbe is *Bacillus thuringiensis* PS74G1.

8. A method for controlling house dust mites which comprise contacting said pests with an acarid-controlling effective amount of a stable lysis$^-$spo$^-$cry$^+$*Bacillus thuringiensis* isolate selected from the group consisting of B.t. PS45B1, B.t. PS24J, B.t. PS94R3 B.t. PS62B1 and B.t. PS74G1, and mutants thereof which retain the property of activity against acarid pests.

* * * * *

UNITED STATES PATENT AND TRADEMARK OFFICE

CERTIFICATE OF CORRECTION

PATENT NO. : 5,350,576

DATED : September 27, 1994

INVENTOR(S) : Jewel Payne, Raymond J.C. Cannon, Angela L. Ralph

It is certified that error appears in the above-indentified patent and that said Letters Patent is hereby corrected as shown below:

Column 1, line 8: Delete "filed Sep. 30, 1991, which is a" and insert -- filed September 30, 1991, now U.S. Patent No. 5,211,946, which is a --.

Column 1, line 18: Delete "toms. A mouse-lethal ct-exotoxin" and insert -- toxins. A mouse-lethal $\alpha$-exotoxin --.

Column 1, line 39: Delete "B. thudngiensis" and insert -- B. thuringiensis --.

Column 1, line 48: Delete "(a.k.a. B.t. tenebdonis, " and insert -- (a.k.a. B.t. tenebrionis --.

Column 1, lines 56-57: Delete "thudngiensis" and insert -- thuringiensis --.

Column 1, line 61: Delete "W. Sctmetter" and insert -- W. Schnetter --.

Column 1, line 68: Delete "thudngiensis" and insert -- thuringiensis --.

Column 2, line 3: Delete "F.R. HaH" and insert -- F.R. Hall --.

Column 2, line 7: Delete "Econ. Entomot." and insert -- Econ. Entomol. --.

Column 2, line 9: Delete "thudngiensis" and insert -- thuringiensis --.

Column 2, line 27: Delete "CrylII" and insert -- CryII --.

Column 2, line 28: Delete "CrylI" and insert -- CryIII --.

Column 3, line 11: Delete "transgenie" and insert -- transgenic --.

UNITED STATES PATENT AND TRADEMARK OFFICE

CERTIFICATE OF CORRECTION

PATENT NO. : 5,350,576

DATED : September 27, 1994

INVENTOR(S) : Jewel Payne, Raymond J.C. Cannon, Angela L Ralph

It is certified that error appears in the above-indentified patent and that said Letters Patent is hereby corrected as shown below:

Column 4, line 39: Delete "Genes and toms." and insert -- Genes and toxins. --.

Column 4, line 53: Delete "acafid activity" and insert -- acarid activity --.

Column 5, line 18: Delete "the art, ff" and insert -- the art, if --.

Column 5, line 25: Delete "identifying tom-" and insert -- identifying toxin- --.

Column 5, line 31: Delete "exemplified toms," and insert -- exemplified toxins, --.

Column 6, line 21: Delete "Pseudornonas," and insert -- Pseudomonas, --.

Column 6, line 35: Delete "competing in the soft" and insert -- competing in the soil --.

Column 6, line 52: Delete "Aureobasidiurn;" and insert -- Aureobasidium; --.

Column 6, line 56: Delete "Eustigrnatophyceae" and insert -- Eustigmatophyceae --.

Column 6, line 61: Delete "Agrobacteriurn" and insert -- Agrobacterium --.

Column 6, line 62: Delete "Rhizobium" and insert -- Rhizobium --.

Column 6, line 63: Delete "AIcaligenes" insert -- Alcaligenes --.

Column 6, line 68: Delete "IGuyveromyces" insert -- Kluveromyces --.

Column 6, line 68: Delete "Aureobasidiurn" and insert -- Aureobasidium --.

Column 7, line 25: Delete "the prolfferative" and insert -- the proliferative --.

UNITED STATES PATENT AND TRADEMARK OFFICE
CERTIFICATE OF CORRECTION

PATENT NO. : 5,350,576

DATED : September 27, 1994

INVENTOR(S) : Jewel Payne, Raymond J.C. Cannon, Angela L. Ralph

It is certified that error appears in the above-indentified patent and that said Letters Patent is hereby corrected as shown below:

Column 9, line 38: Delete "$K_2PO_4$" and insert -- $KH_2PO_4$ --.

Column 9, line 60: Delete "centrigugation" and insert -- centrifugation --.

Column 10, line 8: Delete "thurbtgiensis" and insert --thuringiensis--.

Column 11, lines 21-22: Delete "Agrobacterium tumefaciens or Agobacterium" and insert -- Agrobacterium tumefaciens or Agrobacterium --.

Column 11, line 34: Delete "Agobacterium tumefaciens" and insert -- Agrobacterium tumefaciens --.

Column 11, line 41: Delete "Mot Gen. Genet." and insert -- Mol. Gen. Genet. --.

Column 11, line 43: Delete "The v/r region" and insert -- The vir region --.

Column 11, lines 47-48: Delete "turnefaciens or Agrobacteriurn" and insert -- tumefaciens or Agrobacterium --.

Column 11, line 57: Delete "electropotation" and insert -- electroporation --.

Column 12, line 40: Delete "Dermatophagiodes pteronysinus" and insert -- Dermatophagiodes pteronyssinus --.

Column 33, line 42-43: Delete "Dermatophagodes" and insert -- Dermatophagiodes --.

UNITED STATES PATENT AND TRADEMARK OFFICE

CERTIFICATE OF CORRECTION

PATENT NO. : 5,350,576

DATED : September 27, 1994

INVENTOR(S) : Jewel Payne, Raymond J.C. Cannon, Angela L. Ralph

It is certified that error appears in the above-indentified patent and that said Letters Patent is hereby corrected as shown below:

Column 33, line 46: Delete "B.T. OS45B1, B.t. PS24J, G.t. PS94R3" and insert -- B.t. PS45B1, -- B.t. PS24J, B.t. PS94R3 --.

Column 34, line 50: Delete "B.t. PS94R3 B.t. PS62B1" and insert -- B.t. PS94R3, B.t. PS17, B.t. PS62B1 --.

Signed and Sealed this

Sixth Day of December, 1994

Attest:

BRUCE LEHMAN

Attesting Officer

*Commissioner of Patents and Trademarks*